US00PP36520P2

(12) United States Plant Patent
Coetzee

(10) Patent No.: US PP36,520 P2
(45) Date of Patent: Mar. 4, 2025

(54) GRAPEVINE PLANT NAMED 'NAVSEL 44'

(50) Latin Name: *Vitis vinifera*
Varietal Denomination: NAVSEL 44

(71) Applicant: SPECIAL NEW FRUIT LICENSING LIMITED (SNFL), Peterborough (GB)

(72) Inventor: Gideon Jacobus Nicolaas Coetzee, Rawsonville (ZA)

(73) Assignee: SPECIAL NEW FRUIT LICENSING LIMITED (SNFL), Peterborough (GB)

( * ) Notice: Subject to any disclaimer, the term of this patent is extended or adjusted under 35 U.S.C. 154(b) by 64 days.

(21) Appl. No.: 18/545,833

(22) Filed: Dec. 19, 2023

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 5/08; A01H 5/00; A01H 6/88
See application file for complete search history.

(56) References Cited

U.S. PATENT DOCUMENTS

PP19,912 P2 * 4/2009 Sheehan ..... A01H 6/88 Plt./207
PP20,252 P3 * 9/2009 Sheehan ..... A01H 6/88 Plt./205

* cited by examiner

*Primary Examiner* — June Hwu
(74) *Attorney, Agent, or Firm* — Michael Best & Friedrich LLP

(57) ABSTRACT

'NAVSEL 44' is a new and distinct grapevine plant with novel characteristics that include good fertility, naturally loose bunches, and light muscat flavor. The berries produced by 'NAVSEL 44' are white and seedless with a crunchy and juicy texture and no detectable seed traces. The berries produced by 'NAVSEL 44' are large, weighing 5.4 g/berry on average, and are harvested in mid-July in the Murcia Region (Spain).

1 Drawing Sheet

Latin name of the genus and species: *Vitis vinifera*.
Variety denomination: 'NAVSEL 44'.

BACKGROUND

Described herein is a new and distinct variety of seedless grapevine named 'NAVSEL 44'. The new variety originated from a hybridization performed in Wellington, South Africa in 2010 between 'Sheegene-12' (U.S. Plant Pat. No. 20,252), as the seed parent, and 'Prime Seedless' (not patented), as the pollen parent. Abortive seed traces were embryo cultured and the resulting plant was planted in an evaluation block during 2012. The first evaluation of the fruit produced by 'NAVSEL 44' was performed during 2014. 'NAVSEL 44' was first asexually propagated by field grafting dormant hardwood scions to 1103 Paulsen Rootstock (not patented) in 2014 in Stellenbosch, South Africa. Fruit from the resulting four grafted 'NAVSEL 44' vines was first harvested in 2016. All characteristics and distinctions remain true to form and are established and transmitted through succeeding propagations.

SUMMARY

The following are the most outstanding and distinguishing characteristics of 'NAVSEL 44'. 'NAVSEL 44' produces naturally medium (5.4 g/berry) seedless white (2.5GY7/8) berries. The berries produced by 'NAVSEL 44' have a broad ellipsoid shape with light muscat flavor, and crunchy and juicy texture, that are harvested in mid of July in Murcia, Spain.

'NAVSEL 44' is most similar to 'Sheegene-2' (U.S. Plant Pat. No. 19,912). Nonetheless, the new cultivar can be distinguished from 'Sheegene-2' based at least upon fertility, harvest time, and berry shape. The variety 'NAVSEL 44' has less fertility than 'Sheegene-2' (1.2 vs. 1.4). The harvest period of 'NAVSEL 44' is mid-July whereas the harvest period of 'Sheegene-2' is at the end of July (2 weeks later). The berries produced by 'NAVSEL 44' have a broad ellipsoid shape while the berries produced by 'Sheegene-2' have an ovate shape.

'NAVSEL 44' can be distinguished from its female parent, 'Sheegene-12' (U.S. Plant Pat. No. 20,252), in that the new cultivar is harvested in mid-July while the harvest time of 'Sheegene-12' is in August (3-4 weeks later) in Murcia, Spain. The berries produced by 'NAVSEL 44' are white (2.5GY7/8), whereas the berries produced by 'Sheegene-12' are red. The new variety 'NAVSEL 44' produces berries with an excellent muscat flavor and broad ellipsoid shape, while the variety 'Sheegene-12' produces berries with a neutral flavour and ovate shape.

'NAVSEL 44' can be distinguished from its male parent, 'Prime seedless', in that the new cultivar is harvested in mid-July whilst the harvest time of 'Prime seedless' is at the end of June (2 weeks earlier) in Murcia, Spain. The bunches produced by 'NAVSEL 44' are less compact than the bunches produced by 'Prime seedless' (lax vs. compact). The berries produced by 'NAVSEL 44' have a crunchy texture and thin skin, whereas the berries produced by 'Prime seedless' have a firm texture and medium skin.

BRIEF DESCRIPTION OF THE DRAWINGS OR PHOTOGRAPHS

The accompanying colored photographs illustrate the overall appearance of the 'NAVSEL 44' plant showing the colors as true as it is reasonably possible to obtain in colored reproductions of this type. Colors in the photographs may differ slightly from the color values cited in the detailed botanical description that accurately describe the colors of the plant described herein. These figures are exemplary will vary depending on the plant and distinguishing characteristics.

FIG. 1 shows a photograph starting from top left to right, of a 'NAVSEL 44' primary fruit bunch, a mature upper surface leaf, a secondary fruit bunch, an immature upper leaf, a young shoot, berries (whole, longitudinal cut and cross section) and a floral cluster of a 3-year-old 'NAVSEL 44' plant grown in a field in Murcia, Spain. The colors shown are as true as can be reasonably obtained by conventional photographic procedures.

DETAILED BOTANICAL DESCRIPTION

The following detailed description sets forth the distinctive characteristics of 'NAVSEL 44'. The detailed botanical description was obtained between March and November using 3-year-old plants grown in fields in Murcia, Spain. The color references are to the *Munsell Plant Tissue Color Book,* 2012 edition, Munsell Color.

Classification:
- *Family.*—Vitaceae.
- *Botanical.*—*Vitis vinifera.*
- *Common name.*—Grapevine.
- *Cultivar name.*—'NAVSEL 44'.

Plant:
- *Plant habit and growth.*—Semi-erect.
- *Age at maturity.*—3 years old.
- *Size* (*at maturity*).—Height: 225 cm. Width: 300 cm.
- *Vigor.*—High.
- *Productivity.*—High (1.2 fertility index), around 20 Tn/acre.
- *Rootstock.*—Name of rootstock: 1103 Paulsen Rootstock (not patented). Age of rootstock at time of grafting: one year old.

Trunk:
- *Size.*—Diameter: 4 cm. Height (at measured diameter of 4 cm): 45 cm above the ground.
- *Shape.*—Straight and cylindrical.
- *Surface texture.*—Rough, straight grained with the outer layer easily removed.
- *Bark color.*—Exterior 5YR5/2. Interior 5YR4/4.

Canes:
- *Size.*—Diameter: 8.80 mm. Length: 160 cm.
- *Surface texture.*—Mature cane: smooth, glabrous. Immature cane: very smooth, glabrous.
- *Form* (*woody shoot cross section form*).—Circular; pith in center with diaphragm at nodes.
- *Color.*—Mature: 5 months, 5GY7/8. Immature: 4 weeks, 5GY6/6 (anthocyanins: 10R3/6). Dorsal side of internodes: 5GY7/8; anthocyanins: 2.5R5/6. Ventral side of internodes: 5GY7/8. Dorsal side of nodes: 5GY7/8. Ventral side of nodes: 5GY7/8.
- *Internode length* (*upper mature sun cane*).—13.3 cm.
- *Internode width* (*upper mature sun cane*).—8.6 mm.
- *Node width.*—13.40 mm.

Bud:
- *Bud description.*—Winter bud: rounded, pointed, color 2.5YR3/4. Green bud: rounded and pointed, 5GY6/6 without anthocyanins.
- *Time of bud burst.*—1 March.
- *Time of bud leaf burst.*—7 March.

Tendrils:
- *Form.*—Mostly trifid, smooth, large and think.
- *Size.*—Length: 33.5 cm. Diameter: 3.10 mm.
- *Texture and distribution of tendril at each node beginning at base.*—Smooth, discontinuous, 0000000101010010101001 0010 (0 means no tendril at that node and 1 means there is tendril at the node).
- *Color.*—Mature: 4 weeks, 5GY7/8. Immature: 10 days, 2.5GY6/8.
- *Anthocyanin.*—Mature: not present. Immature: not present.

Growing tips (young shoot):
- *Pubescence.*—Absence.
- *Color.*—2.5GY5/8.
- *Anthocyanin.*—Absent.
- *Shape.*—Fully open.
- *Apex.*—Triangular.
- *Form of tip.*—Fully open.
- *Shoot attitude before tying.*—Semi-erect.

Leaves:
- *Shape.*—Wedge shaped.
- *Apex.*—Pointed.
- *Base.*—Pentagonal.
- *Number of lobes.*—5.
- *Depth of upper lateral sinuses of mature leaves.*—Deep, braced-shaped.
- *Arrangement of lobes of upper lateral sinuses on mature leaves.*—Strongly overlapped.
- *Margin.*—Irregular teeth.
- *Length of teeth on margin.*—2 to 10 mm.
- *Shape of teeth on margin.*—Both sides convex.
- *Texture* (*mature leaf*).—Upper surface: smooth, with a weak goffering of blade. Lower surface: smooth, main veins are raised, glabrous.
- *Size.*—Immature: Length: 10 days, 5.25 cm. Width: 10 days, 5.3 cm. Mature: Length: 4 weeks, 18.9 cm. Width: 4 weeks, 18 cm.
- *Ratio of length/width of teeth* (*mature leaf*).—Small.
- *Color.*—Immature leaf: Upper surface: 5Y 5/6 (without anthocyanins). Lower surface: 2.5 GY5/8. Mature leaf: Upper surface: 7.5GY4/4. Lower surface: 5GY5/4. Autumn coloration: Upper surface: 5Y6/8. Lower surface: 5Y6/6.
- *Venation.*—Pattern: palmate (veins on upper leaf are flat; veins on lower leaf are raised), without anthocyanins coloration, without prostrate hairs on veins. Length of middle vein in mature leaves: 13.375 cm. Color: Upper surface: 2.5GY7/8. Lower surface: 2.5GY8/8.
- *Petiolar sinus.*—Slightly open.
- *Petiole.*—Length: 12.2 cm. Diameter: 3.8 mm. Color: 5GY7/6 (anthocyanins 2.5R5/6).

Floral cluster:
- *General description and location.*—Large, mostly in the 4th and 6th node, 100% with shoulders.
- *Quantity of inflorescences per cluster.*—458.
- *Size.*—Length: 15.20 cm. Width: 10 cm hanging; 16 cm with shoulders spread.
- *Peduncle.*—Length: 4.25 cm.

*Inflorescences*.—Hermaphroditic.
*Stamens*.—5 per flower, straight, 2.85 mm.
*Anthers*.—Small, nondescript.
*Date of bloom*.—Start: 29 April, 50%: 5 May, 100%: 9 May.
*Pollen amount*.—Sparse-medium.
*Calyptra*.—5 segments, complete separation.
*Calyptra color*.—5GY5/10.

Fruit:

*Time of year of commercial harvest and shipment*.—July 20, in Murcia, Spain.
*Time of beginning of berry ripening*.—Early season.
*Keeping quality*.—After 30 days of refrigerated storage there are no symptoms of dehydration, the stems and berries are well preserved. The variety keeps its excellent and muscat flavor, as well as the firmness.
*Cluster* (*primary bunches*).—General size: medium (550 g non tipped, 600 g tipped). Length (without peduncle): 20 cm non tipped; 22 cm tipped. Width: 13.5 cm hanging, 17.6 cm with shoulders spread. Density: lax. Peduncle length: 6 cm. Peduncle diameter: 4.2 mm. Peduncle color: 5GY 6/6. Number of berries per cluster: 129 (on average). Berry: Size: large (5.4 g). Diameter: 20 mm. Length: 22 mm. Shape: broad ellipsoid. Uniformity: very uniform. Brix content: 19.1° Brix. Titratable acidity: 0.46. Skin color (without bloom): 2.5GY7/8. Skin color (with bloom): 2.5GY7/8. Pedicel: Length: 7.5 mm. Diameter: 1.6 mm. Color: 5GY6/6. Strength of attachment to berry: very strong, 15%.
*Cluster* (*secondary bunches*).—General size: small, 140 g. Length (without peduncle): 7.6 cm. Width: 8.2 cm hanging; 10 cm with shoulders spread. Density: lax. Peduncle length: 7.9 cm. Peduncle diameter: 4 mm. Peduncle color: 2.5GY7/6. Number of berries per cluster: 22 (on average). Berry: Size: medium, 4.2 g. Diameter: 17.8 mm. Length: 20.1 mm. Shape: broad ellipsoid. Uniformity: very uniform. Brix content: 18.5° Brix. Titratable acidity: 0.58. Skin color (without bloom): 2.5GY7/8. Skin color (with bloom): 5GY7/8. Pedicel: Length: 7 mm. Diameter: 1.8 mm. Color: 5GY6/6. Strength of attachment to berry: very strong, 10%.

Berry flesh:

*Color*.—2.5GY8/4.
*Anthocyanin color of berry flesh*.—Absent.
*Juice, color*.—2.5GY8/6.
*Juice production*.—High, 43.6%.
*Thickness of skin*.—Thin.
*Flavor*.—Light muscat, neutral-acid.
*Fragrance*.—Neutral.
*Texture*.—Crunchy and juicy (66.1 shores).
*Seeds*.—Seed rudiments, non-detectable.
*Use*.—Table grape.

Shipping quality, storage life, and market use: 'NAVSEL 44' is an early white/green seedless grape variety, with good quality after five weeks of cold storage. Good eating quality with firm berries and a good muscat flavor. Stem quality was good, with no dehydrated stems and no decay observed post-harvest.

*Market use*.—Table grape.

Disease and insect resistance: This cultivar is susceptible to diseases of its species, such as *Erysiphe necator, Plasmopara viticola, Botrytis cinerea, Daktulosphaira vitifoliae, Ceratitis capitata, Planococcus ficus, Planococcus citri*, and *Empoasca vitis*.

Plant hardiness zone or heat/cold resistance: Not determined.

What is claimed is:

1. A new and distinct variety of grapevine plant named 'NAVSEL 44', substantially as herein illustrated and described.

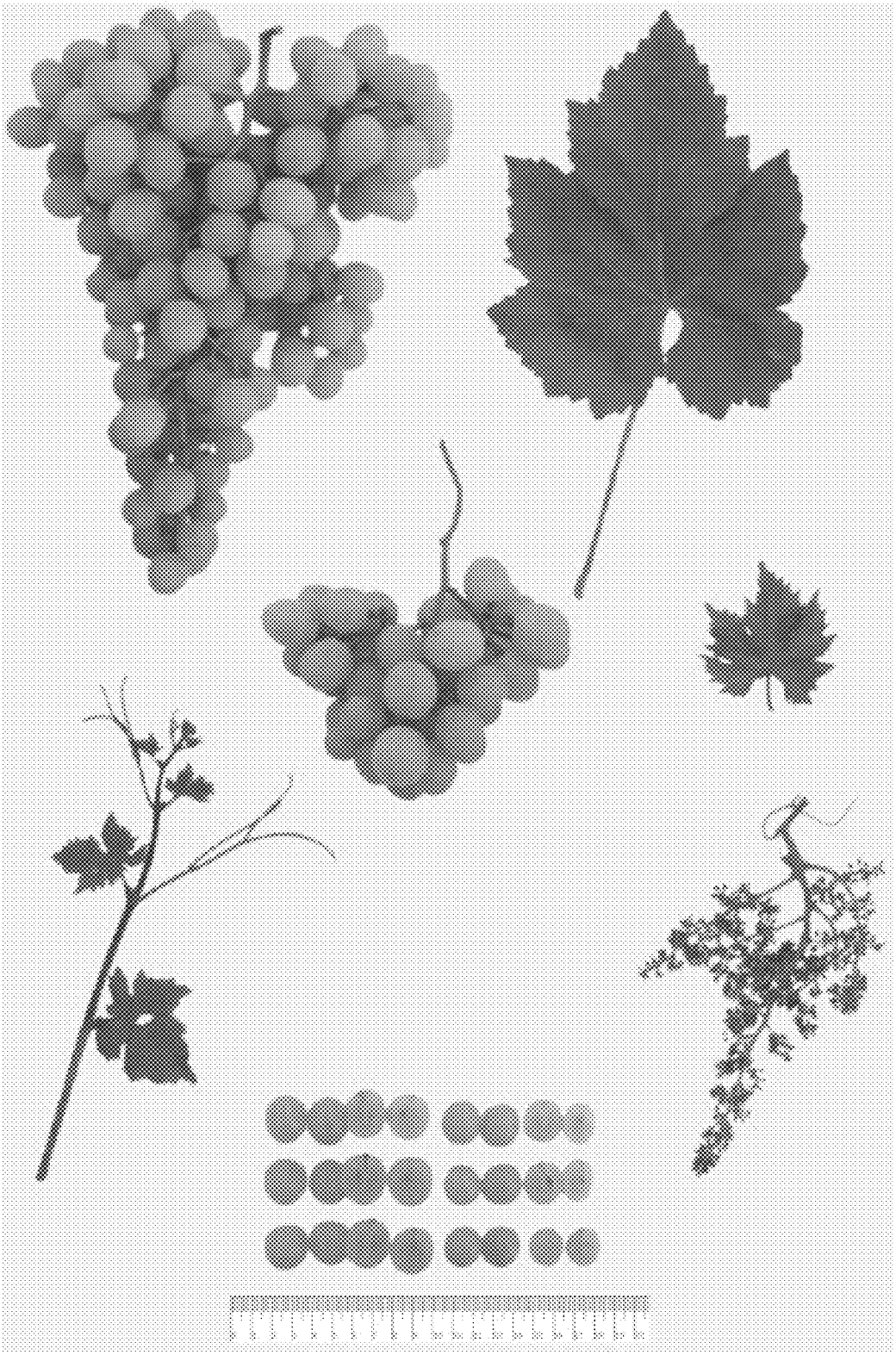

* * * * *